United States Patent
Monks et al.

[11] 4,024,234
[45] May 17, 1977

[54] ORGAN VISUALIZATION

[75] Inventors: Reginald Monks; Anthony Leonard Mark Riley; Gavin Murray Cree, all of Amersham, England

[73] Assignee: The Radiochemical Centre Limited, England

[22] Filed: Feb. 19, 1975

[21] Appl. No.: 550,909

[30] Foreign Application Priority Data

Feb. 20, 1974 United Kingdom ............... 7808/74

[52] U.S. Cl. .................................. 424/1; 250/303; 260/397.2; 424/1.5
[51] Int. Cl.² .................... A61K 43/00; A61N 5/12
[58] Field of Search ............. 424/1, 1.5; 260/397.2; 250/303

[56] References Cited

UNITED STATES PATENTS 3,784,576  1/1974  Counsell ................................ 424/1

OTHER PUBLICATIONS

"Effects of Radiation on the Amino Acid Metabolism of The Superarenal Gland;" Nuclear Science Abstracts, vol. 29, June 1974, No. 27087.

Primary Examiner—Benjamin R. Padgett
Assistant Examiner—Josephine Lloyd
Attorney, Agent, or Firm—Wenderoth, Lind & Ponack

[57] ABSTRACT

Novel selenium-75 derivatives of cholesterol have the formula

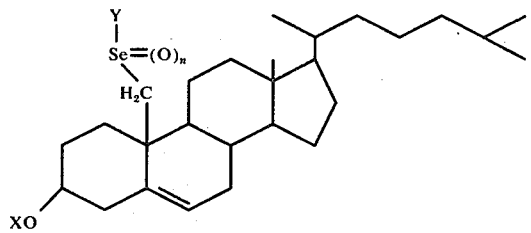

(I) where X is hydrogen or acyl, Y is alkyl and $n$ is 0 or 1. They are useful for visualizing the adrenal glands of mammals.

7 Claims, No Drawings

ORGAN VISUALIZATION

This invention relates to certain selenium-75 labelled steroids, and to their use in visualizing the adrenal glands.

There are no reported instances in the open literature where $^{75}$Se labelled steroids have been used for visualizing the adrenal glands, neither has it been suggested that $^{75}$Se labelled steroids might find application in this respect. There have been reports however describing the preparation of radio-iodinated steroids, and the ability of certain of the compounds to concentrate in the adrenal glands has been demonstrated. When labelled with the γ-emitting $^{131}$I isotope of iodine, such steroids may be used as agents for visualizing the adrenal glands. By way of example, 19-iodocholesterol-$^{131}$I, and its esters have been shown to concentrate in the adrenal glands of rats, dogs and humans and subsequently visualization of human adrenal glands was accomplished.

This invention arises from the idea that $^{75}$Se labelled cholesterol derivatives may be synthesized which exhibit a similar affinity for adrenal tissues. Moreover, $^{75}$Se labelled steroids have certain advantages over their $^{131}$I labelled analogues as demonstrated below.

i. In general aliphatic iodides tend to be unstable, and undergo deiodination. By contrast, aliphatic selenium compounds are frequently quite stable, and do not readily undergo deselenation. For example, 19-iodocholesterol is deiodinated in aqueous and alcoholic media, but 19-methylselenocholesterol is not deselenated under similar storage conditions.

ii. Deiodination may also occur when aliphatic compounds labelled with a radioactive isotope of iodine are administered in vivo. The liberated iodine is concentrated in the thyroid gland which causes unnecessary radiation exposure to that organ. Hence, there is a significant radiation dose to the thyroid gland when 19-iodocholesterol-$^{131}$I is administered in vivo, but there is no significant radiation dose to the thyroid from 19-methylselenocholesterol-$^{75}$Se.

iii. $^{75}$Se is a pure γ-emitter, whereas $^{131}$I has undesirable β emissions associated with its γ-emission. Such β emissions are unsuitable for visualizing the adrenal glands, but they contribute to the radiation dose to the tissue.

iv. $^{75}$Se gives rise to gamma photons which are more suitable for collimation and organ visualization.

v. $^{75}$Se has a longer half-life than $^{131}$I (120 days compared with 8 days). Consequently $^{75}$Se labelled derivatives may be stored for longer periods before an unacceptable decrease in specific activity occurs.

vi. The proportion of photons of suitable energy for photoscanning per disintegration is higher from $^{75}$Se than from $^{131}$I.

vii. A period of at least 6 days is usual between injection of the radioactive nuclide and scanning to allow the nuclide to become located in the adrenal glands. The decay factor over six days is 0.59 for $^{131}$I and 0.96 for $^{75}$Se. For both these reasons (vi) and (vii), a smaller dose of $^{75}$Se than of $^{131}$I suffices to give rise to a desired number of scannable photons, The present invention provides in one aspect a selenium derivative of cholesterol having the general formula:

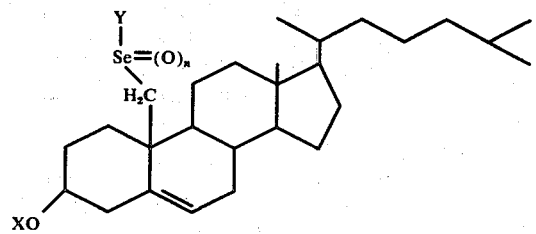

where X is hydrogen or acyl, e.g., acetyl, propionyl or butyryl,
Y is alkyl, e.g., $C_1$ to $C_4$ alkyl, and
$n$ is 0 or 1.

This invention includes the inactive compounds, and also, more particularly, the compounds labelled with $^{75}$Se. The inactive compounds are useful aids in determining the properties of the radioactive compounds.

The present invention also provides a method of visualizing the adrenal glands of a mammal, which method comprises introducing into the live mammal a $^{75}$Se derivative of cholesterol as defined above, allowing the labelled steroid to concentrate in the adrenal glands and observing the radiation emitted by the labelled steroid in the said adrenal glands. When the mammal is an adult human being, the dose administered is generally in the range 0.05 mCi to 5 mCi.

Techniques for introducing a steroid into live mammals and allowing it to concentrate in the desired part, are known in the art and will not be further described here. Observation of the gamma-radiation emitted by the selenium-75, and visualization of the adrenal glands of the mammal where the labelled steroid is concentrated, can be effected with standard equipment.

The compounds may be prepared by reacting 19-iodocholesterol or its esters with suitable alkyl selenides in any convenient solvent which is unattacked by the reagents under the normal reaction conditions.

For example 19-methylselenocholesterol-$^{75}$Se was prepared by reacting excess sodium methyl selenide with 19-iodocholesteryl-3β-acetate in dimethylformamide. The reaction was carried out at room temperature under an atmosphere of nitrogen. In this instance where an excess of sodium methyl selenide was employed, deacetylation at the 3-position and substitution at the 19-position were combined in a single-stage reaction. Alternatively, deacetylation may have been accomplished by a secondary hydrolysis stage, or unesterified products may have been obtained directly from 19-iodocholesterol. 19-methylselenocholesterol has been prepared by this method at high specific activity (3 mCi/mg).

More generally, the selenoalkyl group may be introduced at the $C_{19}$ position of cholesterol by:

i. Displacement of certain $C_{19}$ substituents by selenium-containing nucleophiles.

ii. Reactions with certain metallated intermediates such as the Grignard reagent or lithium salt.

The first method appears to be the more promising.

Nucleophilic substitution at the $C_{19}$ carbon atom

Suitable leaving groups include $Cl^-$, $Br^-$, $I^-$ and certain sulphonates (e.g., p-toluene sulphonate ion). The nucleophiles include the methyl selenide ion ($CH_3Se^-$), diselenide ion ($Se_2^{2-}$), hydrogen selenide ion ($HSe^-$), selenocyanate ion ($Se\,CN^-$), benzyl selenide ion ($\phi CH_2Se^-$), selenosulphate ion ($SeSO_3^=$), and pseudoloselenouronium ion (($NH$)($NH_2$)$CSe^-$). The cations of these compounds are generally alkali metals, ammonium or hydrogen. The methyl selenide ion gives the desired product directly; the others may be converted to the alkylseleno group in subsequent known reactions.

These reactions are similar to known reactions, and suitable conditions will be evident to those skilled in the field. However, it may be necessary to regulate the reaction conditions carefully (e.g., temperature, pH, solvent) in order to exclude or at least minimise side reactions. For example the $\Delta^5$ double bond in cholesterol may participate in the reaction.

EXAMPLES:

$$CH_3.SeNa + ChCH_2.Q \rightarrow ChCH_2.SeCH_3 \quad (a)$$

where Ch is the residue of cholesterol attached to the $CH_2$ group in the 19-position and Q is a leaving group.

The compound $ChCH_2.Q$ has the structural formula:

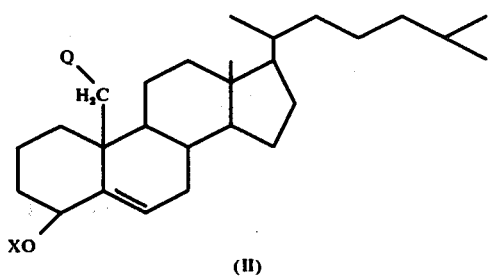

(II)

b) $C_6H_5.CH_2.Se\,Na + ChCH_2.Q \longrightarrow ChCH_2.SeCH_2.C_6H_5$ (1) sodium in liquid ammonia
(2) Methylate (eg. $CH_3I$ or $(CH_3)_2SO_4$)

↓

$ChCH_2.SeCH_3$ c) $KSeCN + ChCH_2.Q \longrightarrow ChCH_2.SeCN$

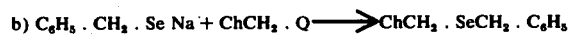

$[ChCH_2.Se]_2 \xrightarrow[(2)\,methylation]{(1)\,reductive\,cleavage} ChCH_2.SeCH_3$ Reductive cleavage can be effected using, for example, dithiothreitol or sodium borohydride.

d) $Na_2Se_2 + ChCH_2.Q$

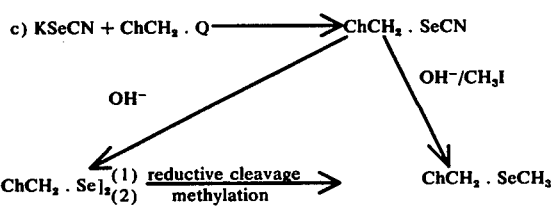

e) $(NH_2)_2C = Se + ChCH_2.Q$ (1) reductive cleavage
(2) methylation

↓

$ChCH_2.SeCH_3$

A wide range of solvents may be used for the above reactions. Among the more useful ones are acetone, isopropanol, and dimethylformamide.

f) $2CH_3.OH + 2Mg + Se \longrightarrow (CH_3.O\,MgSe)_2$ $(CH_3O\,MgSe)_2 + ChCH_2Q \longrightarrow (ChCH_2.Se)_2$ (1) reductive cleavage
(2) methylation

↓

$ChCH_2.SeCH_3$ g) $ChCH_2.Li + Se \longrightarrow ChCH_2.SeLi \xrightarrow{CH_3I} ChCH_2.SeCH_3$ h) $ChCH_2.MgR + Se \longrightarrow ChCH_2.Se\,MgR$

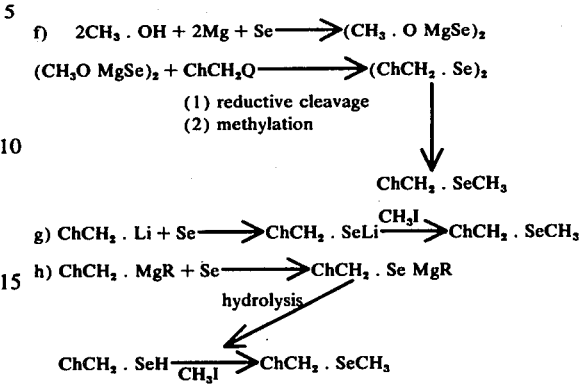

$ChCH_2.SeH \xrightarrow{CH_3I} ChCH_2.SeCH_3$ where R is chloride, bromide or iodide.

3-esterified and selenoxide derivatives of 19-alkyl-selenocholesterol may be prepared by known methods.

The compounds described here have been shown to concentrate preferentially in the adrenal glands of rats with an uptake ratio which would allow a definitive scan of the organ to be made.

The following examples are illustrative of the invention.

EXAMPLE 1

PREPARATION OF 19-METHYLSELENOCHOLESTEROL-[75]Se

Sodium (13.6mg) was added to a reaction vessel containing red selenium (42.5mg; 2Ci) suspended in 15ml of liquid ammonia, the reaction vessel being connected to a vacuum manifold and vented to the atmosphere via a carbosorb/charcoal trap. The reaction mixture was stirred for approximately 15 minutes until a red-brown solution of disodium diselenide was obtained. Methyl iodide (360 μl of 10% v/v solution in pentane) was added to the stirred solution to give an almost colorless solution of dimethyl diselenide. A further quantity of sodium (19mg) was added piecewise until an intense blue coloration was observed. After evaporation of the ammonia a residue of sodium methyl selenide remained. Traces of volatile materials were removed under reduced pressure.

19-iodocholesteryl-3β-acetate (80mg) in dimethylformamide (3ml) was added to the sodium methyl selenide under an atmosphere of nitrogen. After stirring the solution for 20 hours the dimethylformamide was removed under reduced pressure. The residue was dissolved in chloroform (10ml) and the solution then washed with 10% sodium bicarbonate solution (10ml) and water (2 × 6ml). Evaporation of the chloroform afforded a colorless residue of crude 19-methylselenocholesterol-$^{75}$Se which was purified by preparative layer chromatography (Merck Kieselgel 60 $PF_{254}$. Eluent: chloroform, acetone 98:2). The major component of Rf 0.33, as observed by UV fluorescence and autoradiography, was removed from the plate and extracted into ethyl acetate (3 × 3ml). Evaporation of the ethyl acetate afforded a colorless residue of 19-methyl-selenocholesterol-[75]Se (245mCi). TLC on the product (Merck Kieselgel 60 $F_{254}$. Eluent: chloroform, acetone 98:2) followed by autoradiography revealed a major component (97%) at Rf 0.37 and a minor component (3%) at Rf 0.0. The IR spectrum showed the absence of acetoxy groups.

EXAMPLE 2
PREPARATION AND ANALYSIS OF 19-METHYLSELENOCHOLESTEROL

A batch of 19-methylselenocholesterol was prepared by the method described in example 1. T.L.C. and I.R. spectroscopy indicated that the active and inactive compounds were identical.

N.M.R.

$\tau$ 4.47 (broadened S, 1, vinylic proton), $\tau$ 6.47 (multiplet, 1, C$_3$-proton),
$\tau$ 7.20 (dd, 2, J$_{gem}$ = 11 C.P.S., C$_{19}$-protons), $\tau$ 8.06 (S, 3, Se-methyl protons)
$\tau$ 9.12 (S, 6, C$_{26,27}$-protons, -tentative assignment)
$\tau$ 9.18 (S, 3, C$_{21}$-protons, tentative assignment)
$\tau$ 9.23 (S, 3, C$_{18}$-protons, tentative assignment)

| Elemental analysis | %C | %H |
|---|---|---|
| Theoretical | 70.04 | 10.08 |
| Found | 68.71 | 10.07 |

EXAMPLE 3
PREPARATION OF 19-ETHYLSELENOCHOLESTEROL-$^{75}$Se

Sodium (13.5 mg) was added to a reaction vessel containing red selenium (40 mg; 2.36 Ci) suspended in 20 ml of liquid ammonia, the reaction vessel being connected to a vacuum manifold and vented to the atmosphere via a carbosorb/charcoal trap. The reaction mixture was stirred for approximately 15 minutes until a red-brown solution of disodium diselenide was obtained. Ethyl iodide (470 $\mu$l of a 10% $v$/v solution in pentane) was added to the stirred solution to give an almost colourless solution of diethyl diselenide. A further quantity of sodium (25 mg) was added piecewise until an intense blue colouration was observed. After evaporation of the ammonia a residue of sodium ethyl selenide remained. Traces of volatile materials were removed under reduced pressure.

19-iodocholesterol-3$\beta$-acetate (40 mg) in dimethylformamide (2 ml) was added to the sodium ethyl selenide under an atmosphere of nitrogen. After stirring the solution overnight the dimethylformamide was removed under reduced pressure. The residual crude product was dissolved in ethyl acetate (0.3 ml) and purified by preparative layer chromatography (Merck Kieselgel 60 PF$_{254}$. Eluent: chloroform, acetone (98:2). The major UV fluorescent component at Rf approximately 0.35 was removed and extracted into ethyl acetate (3 × 3 ml) to yield 250 mCi of 19-ethylselenocholesterol-$^{75}$Se. TLC on the product (Merck Kieselgel 60 F$_{254}$. Eluent: chloroform, acetone (98:2) followed by autoradiography revealed a single component at Rf 0.42. I.R. spectrum closely resembled that for 19-methylselenocholesterol and showed absence of acetoxy groups.

EXAMPLE 4
PREPARATION OF 19-METHYLSELENOCHOLESTERYL-3$\beta$-ACETATE-$^{75}$Se A solution of 19-methylselenocholesterol-$^{75}$Se (3.2mg; 20mCi) in dry pyridine (1ml) and acetic anhydride (1ml) was left to react at room temperature for 18 hours. Volatile components were then removed under reduced pressure. The residue was dissolved in ethanol (0.25ml) and purified by preparative layer chromatography (Merck Kieselgel 60 PF$_{254}$. Eluent: chloroform, acetone [98:2]). The single UV fluorescent component at Rf approx. 0.4 was removed and extracted into ethyl acetate (3 × 3ml) to yield 17mCi of 19-methylselenocholesteryl - 3$\beta$-acetate-$^{75}$Se, $\nu$max 1233 1746 cm $^{-1}$. TLC (Merck Kieselgel60 F$_{254}$. Elvent: chloroform acetone [98:2]) on the product followed by autoradiography revealed a single component at Rf 0.9. N.B TLC on the crude reaction product using the same system revealed the major component (>90%) at Rf 0.9 and a minor component at Rf 0.0.

EXAMPLE 5
PREPARATION OF 19-METHYLSELENOCHOLESTEROL SELENOXIDE-$^{75}$Se

An aqueous ethanolic solution of 19-methylselenocholesterol (3.2mg, 20mCi) was left to stand or 4 weeks, to permit radiolytic decomposition to take place, and was then evaporated to dryness under reduced pressure. The residue was subjected to thin layer chromatography (Merck Kieselgel 60 F$_{254}$) chloroform; acetone (98:2) followed by autoradiography. The compound having a Rf of 0.0 was recovered.

The title compound can also be made of oxidation of 19-methylselenocholesterol using aqueous hydrogen peroxide.

EXAMPLE 6
TISSUE DISTRIBUTION: 19-METHYLSELENOCHOLESTEROL-$^{75}$Se

50 $\mu$Ci doses of 19-methylselenocholesterol-$^{75}$Se were administered intravenously to rats, which were killed after 6 days, when the radioactivity present in the various organs was measured by scintillation counting. Other rats were sectioned and the radioactivity in the sections located by autoradiography. A high concentration of radioactivity was indicated in the adrenals by both methods.

TABLE 1

Concentration of radioactivity per gram of tissue in the organs of rats 6 days after the intravenous injection of 19-methylselenocholesterol-$^{75}$Se. (mean of four rats)

| | % of injected radioactivity per gram | target/non-target ratio |
|---|---|---|
| Adrenals | 33.63 | |
| Liver | 0.27 | 125 |
| Blood | 0.15 | 222 |
| Kidneys | 0.42 | 80 |
| Testes | 0.14 | 240 |
| Ovaries | 11.28 | 3 |

EXAMPLE 7

TISSUE DISTRIBUTION: 19-METHYLSELENOCHOLESTERYL-3β-ACETATE-$^{75}$Se and 19-ETHYLSELENOCHOLESTEROL-$^{75}$Se 19-methylselenocholesteryl-3β-acetate-$^{75}$Se and 19-ethylselenocholesterol-$^{75}$Se were administered intravenously to four rats in 50 μCi doses. After 6 days the rats were killed and dissected. The activity distribution is expressed below as a target (adrenal) to non-target ratio and the figure is a mean for 2 rats.

Table 2.

| 19-methylselenocholesteryl-3β-acetate-$^{75}$Se | target/non-target ratio |
|---|---|
| A/liver and spleen | 58.1 |
| A/muscle | 47.4 |
| A/blood | 129.3 |
| A/kidney | 33.1 |
| A/gonads | 88.2 |

Table 3.

| 19-ethylselenocholesterol-$^{75}$Se | target/non-target ratio |
|---|---|
| A/liver and spleen | 17.6 |
| A/muscle | 15.0 |
| A/blood | 51.2 |
| A/kidney | 12.4 |
| A/gonads | 22.8 |

EXAMPLE 8

TISSUE DISTRIBUTION: 19-METHYLSELENOCHOLESTEROL SELENOXIDE-$^{75}$Se 19-methylselenocholesterol selenoxide-$^{75}$Se was administered intravenously to rats in 50 μCi doses. After 6 days the rats were killed and dissected. The activity distribution is expressed below as a target (adrenal) to non-target ratio and the figure is a mean for 2 rats.

Table 4.

| 19-methylselenocholesterol selenoxide-$^{75}$Se | Target/non-Target Ratios |
|---|---|
| A/Liver and Spleen | 35.6 |
| A/Muscle | 41.0 |
| A/Blood | 98.6 |
| A/Kidney | 23.3 |
| A/Gonads | 62.1 |

We claim:

1. A selenium derivative of cholesterol having the general formula

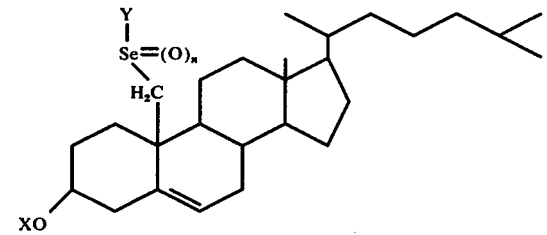

(I)

where X is hydrogen or acyl,
y is alkyl, and
n is 0 or 1.

2. A selenium derivative of cholesterol as claimed in claim 1, labelled with $^{75}$Se.

3. 19-Methylselenocholesterol-$^{75}$Se 4. 19-Ethylselenocholesterol-$^{75}$Se 5. 19-Methylselenocholester yl-3β-acetate-$^{75}$Se.

6. 19-Methylselenocholesterol selenoxide-$^{75}$Se.

7. A method of visualizing the adrenal glands of a mammal, which method comprises introducing into the live mammal a $^{75}$Se derivative of choloesterol as claimed in claim 1, allowing the labelled steroid to concentrate in the adrenal glands, and observing the radiation emitted by the labelled steroid in the said adrenal glands.

* * * * *